United States Patent [19]
Green et al.

[11] Patent Number: 5,814,666
[45] Date of Patent: Sep. 29, 1998

[54] ENCAPSULATED AND NON-ENCAPSULATED NITRIC OXIDE GENERATORS USED AS ANTIMICROBIAL AGENTS

[75] Inventors: Shawn J. Green, Vienna, Va.; Larry K. Keefer, Bethesda, Md.

[73] Assignees: The United States as represented by the Department of Health and Human Services, Washington, D.C.; Entremed, Inc., Rockville, Md.

[21] Appl. No.: 428,632

[22] Filed: Apr. 24, 1995

Related U.S. Application Data

[63] Continuation-in-part of Ser. No. 319,744, Oct. 7, 1994, abandoned, which is a continuation-in-part of Ser. No. 133,601, Oct. 7, 1993, abandoned, which is a continuation-in-part of Ser. No. 867,759, Apr. 13, 1992, abandoned.

[51] Int. Cl.$^6$ .......................... A61K 31/13; A61K 9/127
[52] U.S. Cl. .......................................... 514/611; 424/450
[58] Field of Search .............................. 514/611; 424/450

[56] References Cited

U.S. PATENT DOCUMENTS

| | | | |
|---|---|---|---|
| 4,781,871 | 11/1988 | West, III et al. | 264/4.3 |
| 4,837,028 | 1/1989 | Allen | 424/45 |
| 4,885,173 | 12/1989 | Stanley et al. | 424/440 |
| 4,895,719 | 1/1990 | Radhakrishnan et al. | 514/18 |
| 4,900,719 | 2/1990 | Means et al. | 514/611 |
| 4,954,526 | 9/1990 | Keefer | 514/611 |
| 5,002,964 | 3/1991 | Loscalzo | 514/91 |
| 5,025,001 | 6/1991 | Loscalzo et al. | 514/423 |
| 5,039,705 | 8/1991 | Keefer et al. | 514/427 |
| 5,059,712 | 10/1991 | Griffith | 562/560 |
| 5,091,576 | 2/1992 | Burger | 564/367 |
| 5,116,861 | 5/1992 | Goto et al. | 514/400 |
| 5,155,137 | 10/1992 | Keefer et al. | 514/611 |
| 5,185,376 | 2/1993 | Diodati et al. | 514/611 |
| 5,187,183 | 2/1993 | Loscalzo et al. | 514/400 |
| 5,208,233 | 5/1993 | Keefer et al. | 514/611 |
| 5,212,204 | 5/1993 | Keefer et al. | 514/611 |
| 5,250,550 | 10/1993 | Keefer et al. | 514/611 |
| 5,317,040 | 5/1994 | Goldman | 514/634 |
| 5,366,997 | 11/1994 | Keefer et al. | 514/611 |
| 5,374,710 | 12/1994 | Tsien et al. | 534/552 |
| 5,389,675 | 2/1995 | Christodoulou et al. | 514/492 |
| 5,396,882 | 3/1995 | Zapol | 128/200.14 |
| 5,405,919 | 4/1995 | Keefer et al. | 515/377 |
| 5,428,070 | 6/1995 | Cooke et al. | 514/557 |
| 5,525,357 | 6/1996 | Keefer et al. | 424/486 |
| 5,576,350 | 11/1996 | Wang | 514/565 |
| 5,583,101 | 12/1996 | Stamler et al. | 514/2 |
| 5,622,994 | 4/1997 | Carney et al. | 514/643 |
| 5,663,364 | 9/1997 | Griffith et al. | 548/335.5 |

FOREIGN PATENT DOCUMENTS

| | | |
|---|---|---|
| WO 90/09785 | 9/1990 | WIPO . |
| WO 91/04022 | 4/1991 | WIPO . |
| WO 91/05551 | 5/1991 | WIPO . |
| WO 92/05149 | 4/1992 | WIPO . |

OTHER PUBLICATIONS

Alston, T.A., et al., "Generation of Nitric Oxide by Enzymatic Oxidation of N–Hydroxy–N–Nitrosamines," *J. Bio. Chem.*, vol. 260, No. 7, pp. 4069–4074 (1985).

CA 117(16): 157681e: "Liposome Containing Nitroglycerin," JP 04, 145, 020 (May 19, 1992).

Drago et al., "The Reaction of Nitrogen (II) Oxide with Various Primary and Secondary Amines," *J. of Am. Chem. Soc.*, vol. 83, pp. 1819–1822 (1961).

Drago, "Reactions of Nitrogen (II) Oxide," *Free Radicals in Inorganic Chemistry*, Advances in Chemistry Series, No. 36 (American Chemical Society: Washington, D.C., 1962), pp. 143–149.

Drago, "N–Nitrosohydrooxylamine–N–sulfonates by Metathesis," *Inorganic Syntheses*, vol. V, pp. 120–122 (1957).

Garg et al., "Nitric Oxide–Generating Vasodilators Inhibit Mitogenesis and Proliferation of Balb/C3T3 Fibroblasts by a Cyclic GMP–Independent Mechanism," *Biochem. and Biophys. Res. Comm.*, vol. 171, pp. 474–479 (1990).

Hansen et al., "N–Nitrosation of Secondary Amines by Nitric Oxide Via the 'Drago Complex'," *N–Nitroso Compounds: Occurrence and Biological Effects* (Bartsch et al., eds.) IARC Scientific Publication No. 41(Int'l Agency for Research on Cancer: Lyon, 1982), pp. 21–29.

Hibbs, J.B., et al., "Nitric Oxide: A Cytotoxic Activated Macrophage Effector Molecule," *Biochem. Biophys. Res. Commun.*, vol. 157, No. 1, pp. 87–94 (1988).

Holford et al., "Understanding the Dose–Effect Relationship: Clinical Application of Pharmacokinetic–Pharmacodynamic Models," *Clinical Pharmacokinetics*, vol. 6, pp. 429–453 (1981).

Howard–Flanders, "Effect of Nitric Oxide on the Radiosensitivity of Bacteria," *Nature*, vol. 180, pp. 1191–1192 (1957).

Hrabie, J. A., et al., "New Nitric Oxide–Releasing Zwitterions Derived From Polyamines," *Journal of Organic Chemistry*, vol. 58, pp. 1472–1476 (1993).

Ignarro et al., "Mechanism of Vascular Smooth Muscle Relaxation by Organic Nitrates, Nitrities, Nitroprusside and Nitric Oxide: Evidence for the Involvment of S–Nitrosothiols as Active Intermediates," *J. Pharmacol. Exp. Ther.*, vol. 218, pp. 739–749 (1981).

Ignarro et al., "The Pharmacological and Physiological Role of Cyclic GMP in Vascular Smooth Muscle Relaxation," *Annu. Rev Pharmacol. Toxicol.*, vol. 25, pp. 171–191 (1985).

(List continued on next page.)

*Primary Examiner*—Deborah C. Lambkin
*Attorney, Agent, or Firm*—Leydig, Voit & Mayer, Ltd.

[57] ABSTRACT

This invention relates to compositions capable of releasing nitric oxide and therapeutic methods of use thereof for the treatment of microorganism-related disease states. The composition comprises one or more nitric oxide generators, preferably encapsulated in vesicles, such as liposomes. The compositions are used therapeutically by administration to humans and animals via different routes for the treatment of infectious diseases caused by pathogenic microbes.

26 Claims, No Drawings

OTHER PUBLICATIONS

Ignarro, "Biosynthesis and Metabolism of Endothelium–Derived Nitric Oxide," *Annu. Rev. Pharmacol. Toxicol.,* vol. 30, pp. 535–560 (1990).

Ignarro, "Nitric Oxide: A Novel Signal Transduction Mechanism for Transcellular Communication," *Hypertension (Dallas),* vol. 16, pp. 477–483 (1990).

Kruszyna et al., "Red Blood Cells Generate Nitric Oxide from Directly Acting, Nitrogenous Vasodilators," *Toxicol. Appl. Pharmacol.,* vol. 91, pp. 429–438 (1987).

Kuhn et al., "Endothelium–Dependent Vasodilatation in Human Epicardial Coronary Arteries: Effect of Prolonged Exposure to Glycerol Trinitrate or SIN–1," *J. Cardiovasc. Pharmacol.,* vol. 14 (Suppl. 11), pp. S47–S54 (1989).

Kwon, N.S., et al., "Inhibition of Tumor Cell Ribonucleotide Reductase by Macrophage–Derived Nitric Oxide," *J. Exp. Med.,* vol. 174, No. 4, pp. 761–767 (1991).

Longhi et al., "Metal–Containing Compounds of the Anion $(C_2H_5)_2NN_2O_2{-}$", *Inorganic Chemistry* 2, pp. 85–88 (1963).

Maragos, C.M., et al., "Complexes of NO with Nucleophiles as Agents for the Controlled Biological Release of Nitric Oxide. Vasorelaxant Effects," *Journal Medical Chemistry,* vol. 34, pp. 3242–3247 (1991).

Maragos, C.M., et al., "Nitric Oxide/Nucleophile Complexes Inhibit the In Vitro Proliferation of A375 Melanoma Cells via Nitric Oxide Release," *Cancer Research,* vol. 53, No. 3, pp. 564–568 (1993).

Marletta et al., "Unraveling the Biological Significance of Nitric Oxide," *BioFactors,* vol. 2, pp. 219–225 (1990).

Saavedra, J.E., et al., "Secondary Amine/Nitric Oxide Complex Ions, $R_2N[N(O)NO]^-$. O–Functionalization Chemistry," *Journal Organic Chemistry,* vol. 57, pp. 6134–6138 (1992).

Segal et al., "Morphological Observations on the Cellular and Subcellular Destination if Intravenously Adminstered Liposomes," *Br. J. Exp. Pathol.,* vol. 55, p. 320 (1974).

Smith et al., "Nitroprusside: A Potpourri of Biologically Reactive Intermediates," *Biological Reactive Intermediates IV. Molecular and Cellular Effects and Their Impact on Human Health* (Witmer et al., eds.), Advances in Experimental Medicine and Biology vol. 283 (Plenum Press, 1991), pp. 365–369.

Stuehr, D.J., et al., "Nitric Oxide a Macrophage Product Responsible for Cytostasis and Respiratory Inhibition in Tumor Target Cells," *J. Exp. Med.,* vol. 169, No. 5, pp. 1543–1555 (1989).

Wassef et al., "Complement–Dependent Phagocytosis of Liposomes by Macrophages," *Methods in Enzymology,* vol. 149, pp. 124–134 (1987).

WHO Task Group on Enivronmental Health Criteria for Oxides of Nitrogen, *Oxides of Nitrogen,* Environmental Health Criteria 4 (World Health Organization: Geneva, 1977).

Wilcox et al., "Effects of Cyanide on the Reaction of Nitroprussside with Hemoglobin: Relevance to Cyanide Interference with the Biological Activity of Nitroprusside," *Chem. Res. Toxicol.,* vol. 3, pp. 71–76 (1990).

Wink, D.A., et al., "DNA Deaminating Ability and Genotoxicity of Nitric Oxide and Its Progenitors," *Science,* vol. 254, pp. 1001–1003 (1991).

Zhu et al., "Bactericidal Activity of Peroxynitrite," *Arch. Biochem and Biophys.,* vol. 298, No. 2, pp. 452–457 (1992).

Mancinelli et al., Applied & Environmental Microbiology, vol. 46, No. 1., pp. 198–202, Jul. 1983.

Rockett et al., Infection & Immunity, vol. 59, No. 9, pp. 3280–3283, Sep. 1991.

Incze et al., Applied Microbiology, vol. 27, No. 1, pp. 202–205, Jan. 1974.

ENCAPSULATED AND NON-ENCAPSULATED NITRIC OXIDE GENERATORS USED AS ANTIMICROBIAL AGENTS

CROSS-REFERENCE TO RELATED APPLICATION

This application is a continuation-in-part of U.S. patent application, Ser. No. 08/319,744, filed Oct. 7, 1994, abandoned which is a continuation-in-part of U.S. patent application, Ser. No. 08/133,601, filed Oct. 7, 1993, abandoned, which is a continuation-in-part of U.S. patent application, Ser. No. 07/867,759, filed Apr. 13, 1992, now abandoned.

TECHNICAL FIELD

This invention relates to the treatment of disease, and more particularly to compositions and methods for treating diseases with nitric oxide. In particular, the present invention is directed to the use of compounds which release nitric oxide in aqueous solutions, particularly nitric oxide/nucleophile complexes and their derivatives, to induce cytostasis and cytotoxicity so as to attenuate cell proliferation.

BACKGROUND OF THE INVENTION

Certain infections, particularly those caused by aggressive pathogens that can replicate within cells, have potentially life-threatening consequences for a wide variety of organisms including humans. Many of these aggressive infections involve white cells, called macrophages, that play a major role in engulfing, or phagocytosing, microorganisms such as bacteria. Macrophages play a crucial role in the immune response to several pathologies including neoplastic, bacterial, fungal, parasitic, and viral diseases. Macrophages also maintain homeostatic function through involvement in antigen presentation, removal of aging red blood cells and tissue remodeling.

Therefore, alterations in macrophage function due to any disease process can have severe and potentially life-threatening consequences. For example, in macrophage-based parasitic diseases, invading microorganisms can survive and multiply in the cytoplasm or within intracellular vacuoles of the macrophage, thereby preventing the macrophage from responding appropriately to signals that normally activate the macrophage to kill and eliminate the intracellular pathogen. Instead, the infected macrophage now serves as the vehicle to promote the disease process. Accordingly, diseases that threaten macrophages may have significant impact on the immune response and are therefore potentially lethal.

Macrophage-based diseases include parasitic, fungal, bacterial and viral infections which deleteriously affect macrophages. These diseases account for a tremendous amount of suffering, loss of life, and a large percentage of world health problems. The economic cost of such infections in humans and in domesticated animals is staggering. Current approaches for combating these infections involve parenteral administration of high doses of drugs. Many infectious diseases are resistant to drug therapy (e.g. TB and malaria). For those pathogens which are drug-resistant high doses of drugs are necessary. Additionally, the administered drugs are diluted in the circulatory system before reaching the desired site of action (inside the macrophage), and are also degraded in the liver. These high doses of drugs often cause a metabolic overload in the liver, with subsequent undesirable toxic side effects. There is a great need for new methods of combating macrophage-based diseases.

Several organisms, for example, *Mycobacterium tuberculosis*, Toxoplasma, Leishmania, etc., are phagocytosed by macrophages, and are often concentrated within intracellular organelles called lysosomes. Lysosomes are vesicular structures that are functionally linked to the digestive capability of cells, particularly macrophages that are specialized for phagocytosis. Lysosomes contain high concentrations of hydrolytic enzymes in an acidic environment. Organisms such as *Mycobacterium tuberculosis* can survive and multiply in lysosomes and their progeny phagolysosomes, and transform the macrophage from a disease fighting cell to a disease promoting cell.

Nitric oxide (NO) has recently been implicated in a variety of bioregulatory processes, including normal physiological control of blood pressure, macrophage-induced cytostasis and cytotoxicity, and neurotransmission (Moncada et al., "Nitric Oxide from L-Arginine: A Bioregulatory System," *Excerpta Medica*, International Congress Series 897 (Elsevier Science Publishers B.V.: Amsterdam, 1990); Marletta et al., "Unraveling the Biological Significance of Nitric Oxide," *Biofactors*, 2, 219–225 (1990); Ignarro, "Nitric Oxide. A Novel Signal Transduction Mechanism for Transcellular Communication," *Hypertension (Dallas)*, 16, 477–483 (1990)). A number of compounds have been developed which are capable of delivering nitric oxide, including compounds which release nitric oxide upon being metabolized and compounds which release nitric oxide in aqueous solution.

Those compounds which release nitric oxide upon being metabolized include the widely used nitrovasodilators glyceryl trinitrate and sodium nitroprusside (Ignarro et al., *J. Pharmacol. Exp. Ther.*, 218, 739–749 (1981); Ignarro, *Annu. Rev. Pharmacol. Toxicol.*, 30, 535–560 (1990); Kruszyna et al., *Toxicol. Appl. Pharmacol.*, 91, 429–438 (1987); Wilcox et al., *Chem. Res. Toxicol.*, 3, 71–76 (1990)). Another compound, S-nitroso-N-acetylpenicillamine, has been reported to release nitric oxide in solution and as being effective at inhibiting DNA synthesis (Garg et al., *Biochem. and Biophys. Res. Comm.*, 171, 474–479 (1990)).

Nitric oxide/nucleophile complexes which release nitric oxide in aqueous solution are disclosed in U.S. Pat. Nos. 4,954,526, 5,039,705, 5,155,137, 5,212,204, 5,250,550, 5,366,997, 5,389,675, and 5,405,919 as well as in pending U.S. patent application 08/017,270 (filed Feb. 12, 1993), as being useful cardiovascular agents (see also Maragos et al., *J. Med. Chem.*, 34, 3242–3247 (1991)).

The cytostatic effect of nitric oxide solutions on tumor cells in vitro has been demonstrated. In particular, it has been shown that solutions of nitric oxide inhibit DNA synthesis and mitochondrial respiration of tumor cells in vitro (Hibbs et al., *Biochem. and Biophys. Res. Comm.*, 157, 87–94 (1988); Stuehr et al., *J. Exp. Med.*, 169, 1543–1555 (1989)). Nitric oxide in its pure form, however, is a highly reactive gas having limited solubility in aqueous media (WHO Task Group on Environmental Health Criteria for Oxides of Nitrogen, *Oxides of Nitrogen*, Environmental Health Criteria 4 (World Health Organization: Geneva, 1977)). Nitric oxide, therefore, is difficult to introduce reliably into most biological systems without premature decomposition.

The difficulty in administering nitric oxide can be overcome in some cases by administering nitric oxide pharmacologically in prodrug form. The compounds glyceryl trinitrate and sodium nitroprusside are relatively stable but release nitric oxide only on redox activation (Ignarro et al., *J. Pharmacol. Exp. Ther.*, 218, 739–749 (1981); Ignarro, *Annu. Rev. Pharmacol. Toxicol.*, 30, 535–560 (1990); Kruszyna et al., *Toxicol. Appl. Pharmacol.*, 91, 429–438 (1987); Wilcox et al., *Chem. Res. Toxicol.*, 3, 71–76 (1990)). While this feature may be an advantage in some applications, it can also be a significant liability, as in the development of tolerance to glyceryl trinitrate via the exhaustion of the relevant enzyme/cofactor system (Ignarro et al., *Annu. Rev. Pharmacol. Toxicol.*, 25, 171–191 (1985); Kuhn et al., *J. Cardiovasc. Pharmacol.*, 14(Suppl. 11), S47–S54 (1989)) and toxicity from metabolically produced cyanide during prolonged administration of nitroprusside (Smith et al., "A Potpourri of Biologically Reactive Intermediates" in *Biological Reactive Intermediates IV. Molecular and Cellular Effects and Their Impact on Human Health* (Witmer et al., eds.), Advances in Experimental Medicine and Biology Volume 283 (Plenum Press: New York, 1991), pp. 365–369).

Nitric oxide gas can be formed metabolically from the amino acid L-arginine through the action of the enzyme nitric oxide synthase. Recent evidence shows that direct delivery of nitric oxide kills intracellular pathogens such as *Mycobacterium tuberculosis*. An ability to specifically deliver compounds capable of releasing nitric oxide to the desired site of infection within the macrophage would greatly enhance killing of intracellular pathogens.

It is known that parenterally injected liposomes are rapidly ingested by macrophages, particularly in the liver and spleen, where they are gradually degraded in lysosomal vacuoles (Segal, et al. (1974), *Br. J. Exp. Pathol.* 55, 320). It is also known that liposomes can be taken up by cells by non-receptor-mediated endocytosis, Fc-mediated endocytosis or phagocytosis, or complement-dependent phagocytosis (Wassef and Alving (1987), *Methods in Enzymology* 149, 124).

Liposomes are particles of lipoidal material that can be manufactured from a variety of chemicals and made in different sizes. They are non-toxic, biodegradable lipid spheres. West and Martin teach a method for producing liposomes of specific size no greater than 0.4 microns and concentration of about 250 $\mu$moles/ml (U.S. Pat. No. 4,781,871 (1988), "High Concentration Liposome Processing Method") which is hereby incorporated by reference. Drugs can be encapsulated within liposomes which have been used as delivery vehicles.

Radhakrishnan et al. teach a method and apparatus for aerosolization of liposomes and administration through an inhalation device (U.S. Pat. No. 4,895,719, (1990) "Method and Apparatus for Administering Dehydrated Liposomes by Inhalation" which is hereby incorporated by reference). Nitroglycerine is mentioned among a long list of lipophilic drugs that might be amenable to incorporation in liposomes administered in an aerosol manner. However, neither the '719 nor '871 patent discloses a preparation of liposomes that contain nitric oxide generators that are designed for preferential uptake by macrophages in order to fight macrophage-based disease.

Other patents that mention compounds which produce nitric oxide are concerned primarily with compositions and methods of administration that provide cardiovascular effects since nitric oxide is a potent vasodilator. Keefer and Hrabie in U.S. Pat. No. 5,155,137 (1992) disclose complexes of nitric oxide with polyamines which release nitric oxide in a sustained and controllable fashion to achieve cardiovascular effects. Keefer in U.S. Pat. No. 4,954,526 (1990) and Keefer et al. in U.S. Pat. No. 5,039,705 (1991) disclose the use of stabilized nitric oxide primary amine complexes and secondary amine nitric oxide adducts respectively with cardiovascular activities. Means and Park in U.S. Pat. No. 4,900,719 (1990) disclose the use of S-nitroso compounds, especially S-nitrosothiols, to decrease systemic arterial blood pressure. Stanley and Hague teach methods and compositions for administering drugs, including nitroprusside and nitroglycerin, with renal and cardiovascular activities through a lollipop (U.S. Pat. No. 4,885,173 (1989)).

Loscalzo, in U.S. Pat. Nos. 5,002,964 (1991), 5,025,001 (1991), and 5,187,183 (1993) discloses the use of S-nitroso derivatives of angiotensin converting enzyme inhibitors for the treatment of various pathophysiological diseases. Loscalzo, in U.S. Pat. No. 5,002,964, (1991), teaches the use of S-nitroso derivatives of captopril for cardiovascular effects and for inhibition of platelet aggregation. Diodati and Keefer in U.S. Pat. No. 5,185,376 (1993) disclose the use of nitric oxide complexes for therapeutic inhibition of platelet aggregation.

Goto et al., U.S. Pat. No. 5,116,861 (1992) disclose novel nitrosothiol derivatives for cardiovascular complications.

There remains a need for a method of inhibiting the proliferation of parasites, fungi, bacteria, and other proliferating cells or organisms which can be reliably effected in vivo and which preferably does not require undesirable activation mechanisms.

SUMMARY OF THE INVENTION

The present invention encompasses a method of controlling parasitic infection by inducing cytostasis and/or cytotoxicity among the cells. Specifically, the present invention involves exposing cells to a compound capable of releasing nitric oxide in an aqueous solution, particularly a nitric oxide/nucleophile complex or derivative thereof.

The present invention also encompasses a pharmaceutical composition comprising a pharmaceutically acceptable carrier, including liposomes and polymers, and a therapeutically effective amount of a compound capable of releasing nitric oxide in an aqueous solution, particularly a nitric oxide/nucleophile complex or derivative thereof. The pharmaceutical composition will generally contain an amount of the nitric oxide releasing compound sufficient to induce cytostasis or cytotoxicity among cells exposed to the pharmaceutical composition, and has particular utility in antiparasitic, antifungal, and antibacterial treatments.

It is an object of the invention to provide a method of inhibiting the proliferation of parasites, fungi, bacteria, and other proliferating cells or organisms which can be reliably effected in vivo and which preferably does not require undesirable activation mechanisms.

It is another object of the present invention to provide a pharmaceutical composition useful in carrying out that method.

It is a further object of the invention to provide closed membranous vesicles containing one or more nitric oxide generators for delivering nitric oxide to the interior of target cells.

It is a further object of the invention to provide for selective delivery of nitric oxide generators to macrophages.

Yet another object of the invention is to use liposomes containing nitric oxide generators to treat macrophage-based diseases caused by viruses, bacteria, parasites, and fungi.

A further object of the present invention is to provide for intraarterial administration of liposomes and red blood cells containing nitric oxide generators to deliver high concentrations to specific organs or regions supplied by that artery.

Still another object of the invention is to aerosolize closed membranous vesicles containing nitric oxide generators for administration to the respiratory system through inhalation. An additional object is to administer intracranially liposomes containing nitric oxide generators into the cerebroventricular system to combat bacterial or viral meningitis and parasitic infections.

Another related object is to administer intracranially liposomes containing nitric oxide generators directly into tumors to facilitate intracranial tumor vascularization and regression.

It is another object to inject directly liposomes containing nitric oxide generators into tumors or surrounding tissue, or into vessels supplying tumors, to enhance vascularization of cancerous tissue and access of immune cells to cancerous cells.

Yet another object is to topically apply liposomes containing nitric oxide generators to fight skin diseases including those caused by viruses, bacteria, parasites, and fungi.

A related object is to intradermally or subcutaneously inject liposomes containing nitric oxide generators to fight diseases including those caused by viruses, bacteria, parasites, and fungi.

Still another object of the invention is to administer liposomes containing nitric oxide generators via osmotic pumps.

These and other objects and advantages of the present invention, as well as additional inventive features, will be apparent from the description of the invention provided herein.

DETAILED DESCRIPTION OF THE INVENTION

The present invention is predicated on the discovery that cell proliferation can be attenuated or inhibited by exposing cells to a compound that is capable of releasing nitric oxide in an aqueous solution, specifically a nitric oxide/nucleophile complex or a derivative thereof. The present invention concerns a method of controlling cell proliferation by exposing cells to a compound capable of releasing nitric oxide in an aqueous solution, as well as a pharmaceutical composition which includes a pharmaceutically acceptable carrier and a therapeutically effective amount of a compound capable of releasing nitric oxide in an aqueous solution, particularly a nitric oxide/nucleophile complex or a derivative thereof.

The compounds that are capable of releasing nitric oxide in an aqueous solution in the context of the present invention preferably do so spontaneously upon contacting an aqueous environment, or in response to a shift in the local pH environment, and do not require activation through a redox reaction or electron transfer such as required for glyceryl trinitrate and sodium nitroprusside. Some of the nitric oxide/nucleophile complexes useful in the context of the present invention do require activation by particular means, but only as necessary to free the nitric oxide releasing $X[N(O)NO]^-$ group in the vicinity of the particular cells of interest. As an example, covalent attachment of a protecting group to the anionic $[N(O)NO]^-$ function provides a means of postponing nitric oxide release until the molecule reaches an organ capable of metabolically removing the protecting group. By choosing a protecting group that is selectively cleaved by macrophage- or microorganism-specific enzymes, for example, the action of the nitric oxide/nucleophile complex can be targeted to maximize the desired effect in treating microorganism-dependent disease states. While the nitric oxide releasing compound in the context of the present invention is capable of releasing nitric oxide in an aqueous solution, such a compound preferably releases nitric oxide under physiological conditions.

The compound capable of releasing nitric oxide in an aqueous solution is preferably a nitric oxide/nucleophile adduct, e.g., a complex of nitric oxide and a nucleophile, most preferably a nitric oxide/nucleophile complex which contains the anionic moiety $X[N(O)NO]^-$, where X is any suitable nucleophile residue. The nucleophile residue is preferably that of a primary amine (e.g., $X=(CH_3)_2CHNH$, as in $(CH_3)_2CHNH[N(O)NO]Na$), a secondary amine (e.g., $X=(CH_3CH_2)_2N$, as in $(CH_3CH_2)_2N[N(O)NO]Na$), a polyamine (e.g., X=spermine, as in the zwitterion $H_2N(CH_2)_3NH_2^+(CH_2)_4N[N(O)NO]^-(CH_2)_3NH_2$, or X=(ethylamino)ethylamine, as in the zwitterion $CH_3CH_2N[N(O)NO]^-CH_2CH_2NH_3^+$, or X=3-(n-propyl-amino)propylamine, as in the zwitterion $CH_3CH_2CH_2N[N(O)NO]^-CH_2CH_2CH_2NH_3^+$), or oxide (i.e., $X=O^-$, as in $NaO[N(O)NO]Na$), or a derivative thereof. Such nitric oxide/nucleophile complexes are stable solids and are capable of delivering nitric oxide in a biologically usable form at a predictable rate. The nucleophile is preferably not an entity such as sulfite (e.g., $X=SO_3^-$, as in $NH_4O_3S[N(O)NO]NH_4$), even though the complex is a stable compound, since it is capable of releasing nitric oxide in an aqueous environment only under harsh, nonphysiological conditions.

Other suitable nitric oxide/nucleophile complexes include those having the following formulas:

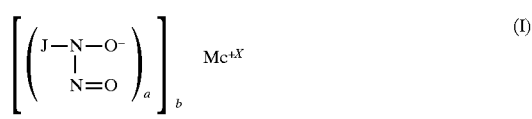

(I)

wherein J is an organic or inorganic moiety, preferably a moiety which is not linked to the nitrogen of the remainder of the complex through a carbon atom, $M^{+x}$ is a pharmaceutically acceptable cation, where x is the valence of the cation, a is 1 or 2, and b and c are the smallest integers that result in a neutral compound, preferably such that the compound is not a salt of alanosine or dopastin, as described more fully in U.S. Pat. No. 5,212,204, which is hereby incorporated by reference in its entirety;

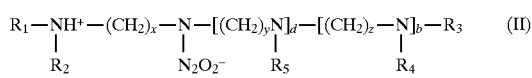

(II)

wherein b and d are the same or different and may be zero or one, $R_1$, $R_2$, $R_3$, $R_4$, and $R_5$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12, as described more fully in U.S. Pat. No. 5,155,137, which is hereby incorporated by reference in its entirety;

(III)

wherein B is

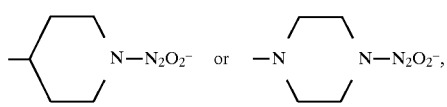

$R_6$ and $R_7$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, f is an integer from 0 to 12, with the proviso that when B is the substituted piperazine moiety

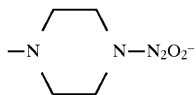

then f is an integer from 2 to 12, as described more fully in U.S. Pat. No. 5,250,550, which is hereby incorporated by reference in its entirety;

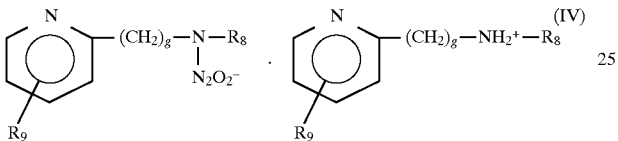

wherein $R_8$ is hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, $R_9$ is hydrogen or a $C_1$–$C_{12}$ straight or branched chain alkyl, and g is 2 to 6, as described more fully in U.S. Pat. No. 5,250,550, which is hereby incorporated by reference in its entirety;

wherein $R_1$ and $R_2$ are independently selected from the group consisting of a straight chain or branched chain $C_1$–$C_{12}$ alkyl group and a benzyl group, preferably with no branch occurring on the alpha carbon atom, or else $R_1$ and $R_2$ together with the nitrogen atom they are bonded to form a heterocyclic group, $M^{+x}$ is a pharmaceutically acceptable cation, and x is the valence of the cation, as more fully described in U.S. Pat. Nos. 5,039,705 and 5,208,233 and U.S. patent application Ser. No. 08/017,270, which are hereby incorporated by reference;

wherein M is a pharmaceutically acceptable metal, or where x is at least two, a mixture of two different pharmaceutically acceptable metals, L is a ligand different from ($R^1R^2N$—$N_2O_2$) and is bound to at least one metal, $R_1$ and $R^2$ are each organic moieties and may be the same or different (preferably where M is copper, x is one, L is methanol, and y is one, that at least one of $R^1$ or $R^2$ is not ethyl), x is an integer of from 1 to 10, x' is the formal oxidation state of the metal M, and is an integer of from 1 to 6, y is an integer of from 1 to 18, and where y is at least 2, the ligands L may be the same or different, z is an integer of from 1 to 20, and K is a pharmaceutically acceptable counterion to render the compound neutral to the extent necessary, as described in U.S. Pat. No. 5,389,675;

wherein R is $C_{2-8}$ lower alkyl, phenyl, benzyl, or $C_{3-8}$ cycloalkyl, any of which R groups may be substituted by one to three substituents, which are the same or different, selected from the group consisting of halo, hydroxy, $C_{1-8}$ alkoxy, —$NH_2$, —$C(O)NH_2$, —$CH(O)$, —$C(O)OH$, and —$NO_2$, X is a pharmaceutically acceptable cation, a pharmaceutically acceptable metal center, or a pharmaceutically acceptable organic group selected from the group consisting of $C_{1-8}$ lower alkyl, —$C(O)CH_3$, and —$C(O)NH_2$, and y is one to three, consistent with the valence of X, as more fully described in U.S. Pat. No. 4,954,526, which is hereby incorporated by reference in its entirety; and

wherein $R_1$ and $R_2$ are independently chosen from $C_1$–$C_{12}$ straight chain alkyl, $C_1$–$C_{12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$ together with the nitrogen atom to which they are bonded form a heterocyclic group, preferably a pyrrolidino, piperidino, piperazino or morpholino group, and $R_3$ is a group selected from $C_1$–$C_{12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_1$–$C_{12}$ unsubstituted or substituted acyl, sulfonyl and carboxamido; or $R_3$ is a group of the formula —$(CH_2)_nON=N(O)NR_1R_2$, wherein n is an integer of 2–8, and $R_1$ and $R_2$ are as defined above; preferably $R_1$, $R_2$ and $R_3$ do not contain a halo or a hydroxy substituent α to a heteroatom, as described in U.S. Pat. No. 5,366,997.

Another class of compounds useful in the present invention are those compounds comprising the nitric oxide/nucleophile adducts bound to a polymer which release nitric oxide in a physiological environment. The present invention also includes pharmaceutical compositions, including implants, patches and the like, incorporating the polymer-bound nitric oxide/nucleophile adduct compositions, and methods of treating biological disorders with polymer-bound nitric oxide/nucleophile adduct compositions. Such compounds are more fully described in U.S. patent application Ser. No. 07/935,565.

By "bound to a polymer," it is meant that the $N_2O_2^-$ functional group is associated with, part of, incorporated with or contained within the polymer matrix physically or chemically. Physical association or bonding of the $N_2O_2^-$ functional group to the polymer may be achieved by coprecipitation of the polymer with a nitric oxide/nucleophile complex as well as by covalent bonding of the $N_2O_2^-$ group to the polymer. Chemical bonding of the $N_2O_2^-$ functional group to the polymer may be by, for example, covalent bonding of the nucleophile moiety of the nitric oxide/nucleophile adduct to the polymer such that the nucleophile residue to which the $N_2O_2^-$ group is attached forms part of the polymer itself, i.e., is in the polymer backbone or is attached to pendant groups on the polymer backbone. The manner in which the nitric oxide-releasing $N_2O_2^-$ functional group is associated, part of, or incorporated with or contained within, i.e., "bound," to the polymer is inconsequential to the present invention and all means of association, incorporation and bonding are contemplated herein.

The present invention also provides a pharmaceutical composition which includes a pharmaceutically acceptable carrier and a polymer having a nitric oxide-releasing $N_2O_2^-$ functional group bound to said polymer. The polymer-bound nitric oxide-releasing $N_2O_2^-$ functional group compositions of the present invention may themselves function as a pharmaceutical composition, as for example, when the polymer-bound composition is in the form of an implant, stent, patch, or the like.

The invention further provides a method of treating biological disorders in which dosage with nitric oxide would be beneficial which comprises administering a composition comprising a polymer and a nitric oxide-releasing $N_2O_2^-$ functional group bound to said polymer in an amount sufficient to release a therapeutically effective amount of nitric oxide.

It has been discovered that incorporation of the $N_2O_2^-$ functional group into a polymeric matrix provides a polymer-bound nitric oxide/nucleophile adduct composition that can be applied with specificity to a biological site of interest. Site specific application of the polymer-bound adduct composition enhances the selectivity of action of the nitric oxide releasing $N_2O_2^-$ functional group. If $N_2O_2^-$ functional groups attached to the polymer are necessarily localized, then the effect of their nitric oxide release will be concentrated in the tissues with which they are in contact. If the polymer is soluble, selectivity of action can still be arranged, for example, by attachment to or derivatization of an antibody specific to the target tissue. Similarly, attachment of $N_2O_2^-$ groups to small peptides that mimic the recognition sequences of ligands for important receptors provides localized concentrated effect of nitric oxide release, as would attachment to oligonucleotides capable of site-specific interactions with target sequences in a nucleic acid.

Additionally, incorporation of the $N_2O_2^-$ functional group into a polymer matrix can reduce the propensity of the nitric oxide/nucleophile adduct for the relatively rapid release of nitric oxide. This prolongs the release of nitric oxide by the $N_2O_2^-$ functional group, and allows for efficient dosing to achieve a desired biological effect so the frequency of dosing can be reduced.

While not being bound to any particular theory, it is believed that longevity of nitric oxide release in the polymer-bound nitric oxide/nucleophile adduct compositions of the present invention is to be attributed to the physical structure of the composition. Thus, it is believed that if the polymer is an insoluble solid, $N_2O_2^-$ groups near the surface of the particle should be available for rapid release while those that are more deeply imbedded are sterically shielded, requiring more time and/or energy for the nitric oxide to work its way into the medium. Unexpectedly, it has been found that increasing positive charge in the vicinity of an $N_2O_2^-$ functional group also tends to increase the half-life of nitric oxide generation. The mechanism of this rate retardation may be attributable simply to repulsive electrostatic interactions, i.e., increasing the number of $H^+$-repelling positive charges in the vicinity of the $N_2O_2^-$ groups inhibits attack of positively charged $H^+$ ions on the $N_2O_2^-$ functional group and slows the rate of its $H^+$-catalyzed decomposition. For example, by attaching amino groups to the polymeric support that are capable of forming these nitric oxide-releasing $N_2O_2^-$ functional group on reaction with nitric oxide, partially converted structures can be produced on less-than-exhaustive treatment with nitric oxide that after exposure to water contain a large number of positively charged ammonium centers surrounding the $N_2O_2^-$ group that electrostatically inhibit the approach of $H^+$ ions capable of initiating nitric oxide loss from the nitric oxide releasing $N_2O_2^-$ functional group.

Any of a wide variety of polymers can be used in the context of the present invention. It is only necessary that the polymer selected is biologically acceptable. Illustrative of polymers suitable for use in the present invention are polyolefins, such as polystyrene, polypropylene, polyethylene, polytetrafluorethylene, polyvinylidene difluoride, and polyvinylchloride, polyethyleneimine, polyethers, polyesters, polyamides such as nylon, polyurethanes, biopolymers such as peptides, proteins, oligonucleotides, antibodies and nucleic acids, starburst dendrimers, and the like.

The physical and structural characteristics of the polymers suitable for use in the present invention are not narrowly critical, but rather will depend on the end use application. It will be appreciated by those skilled in the art that where the polymer-bound nitric oxide/nucleophile adduct compositions of the present invention are intended for topical, dermal, percutaneous, or similar use, they need not be biodegradable. For some uses, such as ingestion or the like, it may be desirable that the polymer of the polymer-bound compositions slowly dissolves in a physiological environment or that it is biodegradable.

The polymer-bound nitric oxide releasing compositions of the present invention will find utility in a wide variety of applications and in a wide variety of forms depending on the biological disorder to be treated. For example, the polymer may be formed into various useful structures such as an implant, patch, stent or the like. Further, by way of illustration, the polymer-bound composition may be incorporated into other polymer matrices, substrates or the like, or it may be microencapsulated, or the like.

The nitric oxide-releasing complexes having $N_2O_2^-$ functional groups, including the compounds described above, may be bound to the polymer support in a number of different ways. For example, the compounds described above may be bound to the polymer by coprecipitation of such compounds with the polymer. Coprecipitation involves, for example, solubilizing both the polymer and the nitric oxide/nucleophile compound and evaporating the solvent.

Alternatively, nitric oxide releasing $N_2O_2^-$ functional groups may be bound to the polymer by formation of a nitric oxide/nucleophile complex of the types and having the formulas of those described above, in situ on the polymer. The $N_2O_2^-$ functional group may be attached to an atom in the backbone of the polymer, or it may be attached to a group pendant to the polymer backbone, or it may simply be entrapped in the polymer matrix. Where the $N_2O_2^-$ functional group is in the polymer backbone, the polymer includes in its backbone sites which are capable of reacting with nitric oxide to bind the nitric oxide for future release. For example, where the polymer is polyethyleneimine, the polymer includes nucleophilic nitrogen atoms which react with nitric oxide to form the $N_2O_2^-$ functional group at the nitrogen in the backbone. Where the $N_2O_2^-$ functional group is a group pendant to the polymer backbone, the polymer contains, or is derivatized with, a suitable nucleophilic residue capable of reacting with nitric oxide to form the $N_2O_2^-$ functionality. Reaction of the polymer which contains a suitable nucleophilic residue, or of the suitably derivatized polymer, with nitric oxide thus provides a polymer-bound nitric oxide-releasing $N_2O_2^-$ functional group.

In another aspect of the invention compositions are prepared that contain encapsulated nitric oxide generators, i.e. the nitric oxide generators are contained within closed membranous vesicles. The term vesicle, as used herein, means a small membrane enclosed sac containing fluid. Vesicles of the present invention include any of the types of liposomes known in the art and red blood cells modified for use as drug delivery vehicles. The compositions may also contain pharmaceutically acceptable excipients, such as buffers, solutions, lotions, oils, gels, emollients and emulsions. In addition to the above-recited compounds, pharmaceutically acceptable salts, zwitterions, and derivatives thereof are also useful in the context of the present invention.

The synthesis of nitric oxide/nucleophile complexes generally involves reacting nitric oxide with suitable nucleophiles and has been described in Drago, "Reactions of Nitrogen(II) Oxide," in *Free Radicals in Inorganic Chemistry*, Advances in Chemistry Series, Number 36 (American Chemical Society: Washington, DC, 1962), pp. 143–149; Hansen et al., "N-Nitrosation of Secondary Amines by Nitric Oxide via the 'Drago Complex,'" in *N-Nitroso Compounds: Occurrence and Biological Effects* (Bartsch et al., eds.), IARC Scientific Publications No. 41 (Int'l Agency for Research on Cancer: Lyon, 1982), pp. 21–29; and Maragos et al., *J. Med. Chem.*, 34, 3242–3247 (1991).

The rate at which the nitric oxide/nucleophile complex releases nitric oxide is dependent on at least the pH of the aqueous solution, the temperature, and the specific nature of the nucleophile. In general, the more alkaline the medium and the lower the temperature, the slower the release of nitric oxide. The nature of the nucleophile influences the rate of nitric oxide release over a considerable range. The effect on cell proliferation of the compound capable of releasing nitric oxide, therefore, can be controlled by appropriate selection of the nitric oxide releasing compound.

The effect of a compound capable of releasing nitric oxide in an aqueous solution on cells is reversible in the sense that the addition of a compound which is capable of removing or scavenging nitric oxide from an aqueous solution by complexing or reacting with nitric oxide can counteract the inhibitory effect of the compound which releases the nitric oxide. The effect on cell proliferation of the compound capable of releasing nitric oxide, therefore, can be further controlled by use of such a nitric oxide scavenger compound in an appropriate quantity.

While the method of the present invention can be practiced in vitro, it has particular usefulness in in vivo applications. The present inventive method, therefore, includes the administration to an animal, particularly a human, of a therapeutically effective amount of a compound capable of releasing nitric oxide in an aqueous solution, particularly a nitric oxide/nucleophile complex or derivative thereof. The use of such a compound in treating animals, particularly humans, circumvents the disadvantages of the use of pure nitric oxide, aqueous solutions of nitric oxide, and compounds which release nitric oxide but require undesirable activation mechanisms. Furthermore, embodiments of the invention capable of specifically targeting the delivery of nitric oxide generating compounds and of modulating the rate of generation of nitric oxide are particularly useful for localized therapeutic treatments. As regards the in vivo use of the present inventive method, a nitric oxide releasing compound in the context of the present invention can be administered in any suitable manner, preferably with pharmaceutically acceptable carriers.

One skilled in the art will appreciate that suitable methods of administering a nitric oxide releasing compound in the context of the present invention to an animal are available, and, although more than one route can be used to administer a particular compound, a particular route can provide a more immediate and more effective reaction than another route. Pharmaceutically acceptable carriers are also well-known to those who are skilled in the art. The choice of carrier will be determined in part by the particular compound, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The nitric oxide releasing compounds in the context of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compound employed and the condition of the animal, as well as the body weight of the animal to be treated. The size of the dose also will be determined by the existence, nature, and extent of any adverse side-effects that might accompany the administration of a particular compound.

In the treatment of some individuals with the pharmaceutical composition of the present invention, it may be desirable to utilize a "mega-dosing" regimen. In such a treatment, a large dose of the pharmaceutical composition is administered to an individual, time is allowed for the active compound, i.e., the nitric oxide releasing compound, to act, and then a suitable reagent, e.g., a nitric oxide scavenger, is administered to the individual to render the active compound ineffective.

The desirable extent of the inhibition of cell proliferation rate will depend on the particular condition or disease being treated, as well as the stability of the patient and possible side-effects. In proper doses and with suitable administration of certain compounds, the present invention provides for a wide range of inhibitory effects on the normal cell proliferation rate, e.g., from little inhibition to essentially full inhibition.

The cytostatic activity of a nitric oxide/nucleophile complex is generally related to the rate and extent of nitric oxide release. It is believed that those compounds which release nitric oxide slowly, such as spermine-bis(nitric oxide) adduct monohydrate and 3(n-propylamino)propylamine bis (nitric oxide) adduct, are more potent inhibitors of DNA synthesis than compounds which release nitric oxide more quickly, such as diethylamine-bis(nitric oxide) adduct sodium salt, isopropylamine-bis(nitric oxide) adduct sodium salt, and sodium trioxodinitrate(II) monohydrate (also known as "Angeli's salt"). It is also believed that a sustained exposure to moderate amounts of nitric oxide has a longer lasting effect than a brief exposure to a greater concentration of nitric oxide. Moreover, the number of molecules of nitric oxide released by a single nitric oxide/nucleophile complex, which will generally vary up to two per [N(O)NO] moiety, apparently affects the potency of the nitric oxide/nucleophile complex, with compounds which release more nitric oxide per molecule having a greater cytostatic effect.

The cytostatic effect of a nitric oxide/nucleophile complex is also dependent on factors in addition to the rate and extent of nitric oxide release. Such factors include specificity of the delivery of nitric oxide generating compounds to localized sites, the mechanism by which the compound degrades, the degree of uptake by the exposed cells, and the affinity for cellular constituents. For example, spermine binds DNA which may play a role in the nitric oxide/spermine complex having a high cytostatic effect on tumor cells. The present invention also has usefulness in prophylactic treatments.

The present invention provides nitric oxide generator-containing compositions and methods of using such compositions that are particularly useful for the treatment of infectious diseases by administering the nitric oxide generator-containing compositions to a human or animal suffering from the disease. The administered nitric oxide generator-containing compositions produce localized and high concentrations of nitric oxide to assist in the killing of infectious pathogens such as parasites, viruses, fungi, protozoa and bacteria.

More particularly, the present invention includes a therapeutic nitric oxide generator-containing composition for treating disease comprising vesicles impregnated with one or more nitric oxide generators and a therapeutic method for treating a disease comprising the step of administering to a human or animal suffering from a disease caused by an infectious microbe an amount of a composition comprising vesicles impregnated with one or more nitric oxide generators effective for killing the infectious microbe.

When nitric oxide generators contact inflammatory cells, such as macrophages, or inflamed areas of tissues, it is believed that the local inflammatory environment triggers the generation and release of nitric oxide. Without wanting to be bound by the following theory, it is believed that a localized change in pH or the presence in high concentration of esterases and hydroxylases at the inflammatory site triggers the formation of nitric oxide by the nitric oxide generator. The localized delivery and high concentration of nitric oxide thus produced damages or destroys harmful and infectious cells at the site of inflammation.

Desirable nitric oxide generators used in the encapsulated and non-encapsulated compositions of the present invention include but are not limited to nitric oxide generators such as SPER/NO, DETA/NO, V—DEA/NO, S—DEA/NO, MOM—DEA/NO, acetoxy-DEA/NO, DEA/NO, SULFI/NO, OXI/NO, A-DEA/NO, M-DEA—NO, HE—DEA/NO, A—IPA/NO, CEM—IPA/NO, BE—DEA/NO, M—IPA/NO, P—DEA/NO, E—DEA/NO, MOM—IPA/NO, and HP—DEA/NO, and combinations thereof. These compounds are more fully described in Table 1. Desirable compounds for use in the present invention include the spontaneous nitric oxide generator DETA/NO and the more stable nitric oxide generator MOM—DEA/NO.

Current therapeutic approaches to treating microbial infections involve the parenteral administration of drugs in high doses that often produce undesirable toxic side effects. Parenteral administration also dilutes the amount of drug that reaches the desired site of action. In contrast, the administration of compositions containing nitric oxide generators eliminates these problems by assuring a high concentration of nitric oxide specifically within macrophages or at sites of inflammation. This targeted delivery of nitric oxide allows lower total dosages to be administered, thus reducing non-specific side effects, without loss of efficacy.

TABLE 1

Chemical Formula of Selected Nitric Oxide Generators

| Name | Formula | Formula Weight | Half-life[1] |
|---|---|---|---|
| SPER/NO | Spermine.2(NO).H$_2$O | 280 | 39 min |
| DETA/NO | H$_2$NCH$_2$CH$_2$N—[CH$_2$CH$_2$NH$_3$]+[N(O)NO]— | 163 | 20 hr |
| V-DEA/NO | Et$_2$NN(O)=NOCH=CH$_2$ | 159 | stable |
| S-DEA/NO | Et$_2$NN(O)=NOSO$_2$NMe$_2$ | 240 | 30 min |
| MOM-DEA/NO | Et$_2$NN(O)=NOCH$_2$OMe | 177 | 5 days |
| acetoxy-DEA/NO | Et$_2$NN(O)=NOCH$_2$OAc | 205 | stable |
| DEA/NO | Et$_2$N[N(O)NO]Na | 155 | 2 min |
| SULFI/NO | NH$_4$O$_3$S[N(O)NO]NH$_4$ | 176 | 7 min[2] |
| OXI/NO | NaO[N(O)NO]Na.H$_2$O | 140 | 2 min |
| A-DEA/NO | Et$_2$NN(O)=NOCH$_2$CH=CH$_2$ | 173 | stable |
| M-DEA-NO | Et$_2$NN(O)=NOMe | 147 | stable |
| HE-DEA/NO | Et$_2$NN(O)=NOCH$_2$CH$_2$OH | 177 | stable |
| A-IPA/NO | $^i$PrHNN(O)=NOCH$_2$CH=CH$_2$ | 159 | stable |
| CEM-IPA/NO | $^i$PrHNN(O)=NOCH$_2$CO$_2$Et | 205 | stable |
| BE-DEA/NO | Et$_2$NN(O)=NOCH$_2$CH$_2$Br | 241 | stable |
| M-IPA/NO | $^i$PrHNN(O)=NOMe | 133 | stable |
| P-DEA/NO | Et$_2$NN(O)=NOPr | 175 | stable |
| E-DEA/NO | Et$_2$NN(O)=NOEt | 161 | stable |
| MOM-IPA/NO | $^i$PrHNN(O)=NOCH$_2$OMe | 163 | stable |
| HP-DEA/NO | Et$_2$NN(O)=NOCH$_2$CHOHMe | 191 | stable |

[1]At pH 7.4 and 37° C.
[2]Generates no nitric oxide.

Liposomes are a desirable vehicle for administering nitric oxide generators because they are ingested by macrophages. Liposomes can be made by any method for making liposomes known in the art. These vesicles may be impregnated with any of the above-described nitric oxide releasing compounds or combinations thereof. The term "impregnated", as used herein, means that one or more of the nitric oxide generator compounds is placed within the lumen or membrane of the liposome. The term "impregnated" is synonymous and used interchangeably with the term "encapsulated."

After administration of the vesicles to the human or animal in need of treatment, the nitric oxide generators undergo a chemical reaction to form nitric oxide, preferably at the site of inflammation or within macrophages, a location where infectious microbes commonly are found within the body. Inflammatory macrophages exhibit high phagocytic activity which may act to concentrate nitric oxide generator-containing vesicles, enhancing the therapeutic efficacy of the nitric oxide generated. Once liposomes bind to the macrophage surface, they are engulfed and internalized in phagolysosomes. The pH environment of phagolysosomes is approximately pH 5–6. The acidic pH promotes release of nitric oxide from the nitric oxide generator. The nitric oxide so produced kills or damages the pathogen, thus reducing or eliminating the microbial infection. When the vesicles are selectively and preferentially taken up by macrophages, the production of nitric oxide often may be further enhanced within the macrophage by the action of enzymes.

Red blood cells (RBC), optionally modified to enhance their uptake by macrophages, are impregnated with nitric oxide generators. Alteration of the phosphatidyl serine content of red blood cell membranes enhances their uptake by macrophages. Red blood cells are loaded with nitric oxide generators according to methods known in the art. For example, RBCs can be made leaky in the presence of nitric oxide generators and the loss of integrity of the cell membrane permits the nitric oxide generators to enter the lumen of the cells. For example, RBC's may be loaded with nitric oxide generators using electroporation techniques well known in the art.

Aging red blood cells are normally phagocytosed by macrophages. According to the present invention, delivery of nitric oxide generators by red blood cells is an effective method for combating splenic disease. As for the liposomes described above, phagocytosis of the RBC enhances production of free nitric oxide within the macrophage. For example, red blood cells encapsulating nitric oxide generators can be delivered via the splenic artery to maximize their uptake into the spleen.

Nitric oxide generator-containing vesicles are administered via several different routes including, but not limited to, the following; intravenous, intraperitoneal, intracranial, inhalation, topical, transdermal, subcutaneous, and also by injection into tumors. Administration takes the form of direct injection, infusion, release from osmotic pumps, and release from subcutaneous implants. For example, administration through the aerosol route is highly beneficial to humans or animals with pulmonary infections. Various bacterial, protozoan, fungal, viral, and parasitic infections of the respiratory system that involve macrophages are attacked in this fashion.

Skin diseases caused by bacteria, viruses, fungi, protozoa and parasites may be treated by topical administration of nitric oxide generator-containing compositions, such as liposomes encapsulating nitric oxide generators or non-encapsulated nitric oxide generators. An example of such a skin disease is cutaneously erupting neural viruses, such as Herpes.

Following uptake of liposomes or red blood cells that contain nitric oxide generators by macrophages, the nitric oxide generators undergo chemical modification within the macrophage to produce free nitric oxide. The resultant generation of nitric oxide occurs within lysosomes and is extremely effective in killing intracellular pathogens. This invention may also provide therapeutic treatment for otherwise untreatable diseases.

The liposome compositions and methods described in this invention are employed for a variety of viral, bacterial, fungal, and parasitic infections. Some of these include, but are not limited to *Mycobacterium tuberculosis, toxoplasmosis*, AIDS, and diseases caused by Leishmania and *Cryptococcus neoformans*.

The following examples are illustrative, but not limiting, of the composition, the method of making and the method of administering the invention. Additional modifications for various conditions encountered in the use of this invention that are obvious to those skilled in the art are within the scope and spirit of the invention.

EXAMPLE I

This Example illustrates the formation of a polymer containing nitric oxide-releasing $N_2O_2^-$ groups that are attached to nucleophile residues pendant on the polymer backbone.

A slurry of 3.0 g chloromethylated polystyrene (1% divinylbenzene; 1.09 mEq Cl per gram; 200–400 mesh; Polysciences, Inc., Warrington, Pa.) in 20 mL n-propyl-1,3-propanediamine was warmed to 60° C. in an oil bath and swirled periodically for 5 days. The polymer was then filtered, washed repeatedly with water then methanol and finally dichloromethane and dried in vacuo for 24 hrs. Elemental analysis showed this material to be 2.21% nitrogen indicating that approximately 80% of the chlorines had been replaced by propylpropanediamino groups.

A slurry of 1.0 g of the resulting aminopolystyrene in 50 mL acetonitrile was placed under 5 atmospheres nitric oxide in a Parr apparatus and shaken intermittently for 3 days. This was filtered and dried in vacuo to yield 0.84 g of cream colored polymer. The elemental analysis suggested that approximately one-third of the amino side chains became attached to $N_2O_2^-$ groups under these conditions.

Using the procedure of Maragos et al. (J. Med. Chem. 34, 3242–3247, 1991) it was demonstrated that nitric oxide can be recovered from the polymer described in this Example. The amount of nitric oxide regenerated when the polymer of Example I was treated with acid was measured with a chemiluminescence detector. The solid sample was placed in a reactor vessel, which was then purged continuously with helium such that the effluent gases were swept into a nitric oxide-selective Thermal Energy Analyzer Model 502 (Thermo Electron Corp., Waltham, Mass.). Only small amounts of nitric oxide were evolved from the solid itself, but when 2 mL of 10 mM sulfuric acid was injected via a septum, a sudden pulse of nitric oxide appeared. Integration of this apparently first order generation of nitric oxide over time indicated that 11 nmol of nitric oxide was recovered from 1 mg of polymer.

The reaction was repeated using 10 mM phosphate buffer at pH 7.4 in place of the sulfuric acid to verify the slow release of nitric oxide at physiological pH. The chemiluminescence detector revealed that nitric oxide was generated very much more slowly.

EXAMPLE II

This Example illustrates the preparation of a polymer-bound nitric oxide/nucleophile complex by coprecipitation of a monomeric form thereof with a polymer.

One gram of polymer [poly(lactide/glycolide, (50:50) from MediSorb] was dissolved in 2 ml of THF. To the solution was added 300 mg of $[H_2N(CH_2)_2]_2N—N_2O_2H$, zwitterionic form, and the mixture was stirred under an argon stream to remove solvent slowly until the mixture became too viscous to stir. The mixture was then placed in a vacuum oven (ca 1 mm) at 30° C. for 5 hours to remove the residual solvent. The mixture was finally pressed on a carver press at 20,000 lbs. at 140° F. for 5 minutes. A film of 1"×1" with thickness of 44 mills was thus prepared. Using the procedure described above, nitric oxide was recovered from this polymer on treatment with acid at the rate of 8 nmol/mg.

EXAMPLE III

This Example illustrates the preparation of a polymer-bound nitric oxide/nucleophile adduct in which the $N_2O_2^-$ group is bound directly to an atom in the polymer backbone.

A slurry of 10.0 g polyethyleneimine on silica gel (Aldrich) in 150 mL acetonitrile was stirred for 3 days under a nitric oxide pressure of 75–80 psig. The resulting orange solid was filtered, washed with $CH_3CN$ then ether, and dried in vacuo for 6 h. Using the procedure described above, nitric oxide was recovered from this polymer on treatment with acid at the rate of 3 nmol/mg.

EXAMPLE IV

Method of preparation of liposomes with nitric oxide generators.

1. Preparation of liposomes.

Liposomes are prepared by methods known in the art. Generally liposomes are prepared by dissolving the lipids that are to constitute the liposome membrane in a solvent such as chloroform. Other solvents, or solvent combinations, such as chloroform and methanol, may be used to dissolve the lipids. Liposomes may contain any combination of a number of lipids, including cholesterol, phosphatidylcholine, dimyristoyl phosphatidylcholine, phosphatidylserine, phosphatidic acid, phosphatidylinositol, phosphatidylethanolamine, cardiolipin, and lecithin. Other components such as glycolipids and lipopolysaccharides may also be used as components of the liposome membrane to make the liposome appear foreign and, therefore, antigenic. Examples of possible glycolipids include gangliosides and digalactosyl diglyceride. An example of a possible lipopolysaccharide is lipid A. Making the liposome antigenic may concentrate liposomes at sites of inflammation and promote uptake of the liposome by immune cells such as macrophages.

Solutions of the desired lipids are mixed in the appropriate ratios to obtain the proper liposome lipid membrane. For example, liposomes may contain phospholipid and cholesterol in a ratio of 1:0.75, which approximates the ratio of phospholipid to cholesterol found in RBCs. Liposomes containing in their membrane phosphatidylcholine and cholesterol in the range of 1:1 to 1:2.5 are also routinely prepared. The lipid solutions are combined in a volume suitable to permit thorough agitation; generally a ten fold greater volume than the anticipated final volume may be used. Solvent is removed, e.g. by rotary evaporation under vacuum. The dried lipids are resuspended in an encapsulating solution, which contains the nitric oxide generator to be trapped within the liposome, by vigorous agitation such as vortexing.

The liposomes that result are multilamellar. Prior to using the liposomes unencapsulated material may be washed away, for example by dialysis or gentle centrifugation. A more detailed description follows.

Encapsulation of Nitric Oxide Generators

Liposomes employed for encapsulation of nitric oxide (NO) generators consisted of dimyristoylphosphatidylcholine (DMPC): dimyristoylphosphatidylglycerol (DMPG): cholesterol, in mole ratios of 9:1:7.5, respectively. Lipids were aliquotted into glass, pear-shaped flasks and the bulk of the chloroform solvent was removed by rotary evaporation. Trace solvent was removed by vacuum desiccation. NO generators were dissolved in ice-cold 0.2 molar carbonate/bicarbonate, pH 9.65, to a final concentration of 0.3 molar and passed through a 0.2 micron filter. NO generators were then added to the dry lipid shells and the mixtures were vortexed vigorously for 1 minute to form the liposomes. Mixtures were incubated on ice for 1 hour. Liposomes were then washed twice with 20 volumes of carbonate bicarbonate buffer, pH 9.65, by centrifugation. Liposome pellets were resuspended to 100 mM with respect to total phospholipid. Encapsulation efficiency was improved by 1) use of higher NO generator concentrations (300 mM, compared to 200 mM previously), and 2) higher phospholipid concentrations (100 mM compared to 10 mM previously). We suspected that higher buffer pH would stabilize the generators and we routinely increase phospholipid concentration when encapsulation efficiency needs improvement.

TABLE 2

Effect of Buffer Composition on Efficiency of Liposome Encapsulation of NO Generators

| NO Generator | *PBS: 200 mM NO-generator 10 mM PL | †Bicarb: 300 mM NO-generator: 100 mM PL |
| --- | --- | --- |
| SPER/NO | 0.60 | 14 |
| DETA/NO | 1.4 | 16 |
| MOM-DEA/NO | 0.06 | 17 |
| Acetoxy-DEA/NO | 0.40 | 74 |

*PBS, pH 7.4, using 200 mM NO-generator encapsulated in 10 mM phospholipid (PL).
†0.2 M bicarbonate, pH 9.65, using 300 mM NO-generator encapsulated in 100 mM phospholipid.

By increasing the amount of phospholipid (10 to 100 mM) and increasing both the pH (7.4 to 9.65) of the diluent and the amount of the NO generator in the diluent (200 to 300 mM), we were able to significantly 'trap' larger amounts of NO donors or generators in the liposome preparations. The above is representative of three experiments. These preparations were subsequently used in animal studies.

Quantitation of Encapsulated Nitric Oxide Generators

In another series of experiments, we were interested in validating our method for measuring the amount of NO generator in the liposomes. The quantitation of encapsulated NO generators was carried out using a Perkin-Elmer dual-beam spectrophotometer programmed for second derivative quantitative scanning. Each NO generator was scanned to determine the precise wavelengths for second derivative scanning. Standard curves were generated for each NO generator and used for quantitating liposome-encapsulated NO generators. For the actual quantitative scan of the encapsulated NO generators, liposome preparations containing either NO generator or buffer were extracted and dilutions of the extracts were measured for the NO generators. A preparation of liposomes without NO generators (control liposomes) was placed in the reference cuvette to correct for the absorbance due to liposomes, and the samples were scanned from 280 to 220 nm using the predetermined wavelengths for second derivative calculation. Results were calculated by the software provided with the spectrophotometer, as modified by the users. To test the reliability of these measurements, we scanned solutions of four NO generators using this method (D2 Scan) and then sent aliquots to chemists at the Frederick Cancer Research and Development Center (FCRDC) where the samples were quantified by direct absorbance using known extinction coefficients (Abs. Scan). Results are given in the table below:

TABLE 3

| NO Generator | D2 Scan | Abs. Scan |
|---|---|---|
| SPER/NO | 0.278 | 0.266 |
| DETA/NO | 0.273 | 0.272 |
| MOM-DEA/NO | 0.306 | 0.295 |
| Acetoxy-DEA/NO | 0.068 | 0.407 |

Values are expressed as mM.

The data suggest that the D2 scan is a valid method for measuring NO generators with the exception of acetoxy-DEA/NO. In particular, the two methods gave comparable results for the preferred compounds, SPER/NO and DETA/NO.

Stability of Liposomes using High-pH Buffer

In another series of experiments, we were interested in assessing the stability of liposomes containing NO generators. Preparations were assessed for $NO_2^-$ accumulation in liposome pellets at 24 and 48 hours after encapsulation. Pellets were then bath sonicated to release encapsulated $NO_2^-$. Fluids were assayed for $NO_2^-$ by the Griess calorimetric reaction and expressed as mM. The initial concentration of NO generator was 200 mM.

TABLE 4

| NO Generator | Pellet, 24 Hours | Pellet, 48 Hours |
|---|---|---|
| SPER/NO | 32.372 | 33.968 |
| DETA/NO | 7.858 | 9.22 |
| MOM-DEA/NO | 0.247 | 0.167 |
| Acetoxy-DEA/NO | 0.372 | 0.334 |
| Control | 0 | 0 |

These results suggest that substantial amounts of NO are retained by the liposome preparations over a 24 hour period when stored in the bicarbonate buffer at room temperature.

Stability of Nitric Oxide Generators

In general, nitric oxide generators are stabilized by storage at high pH (10 mM NaOH) and low temperature (−20° C.). To test the stability of four nitric oxide generators, each generator was dissolved in PBS (neutral buffer) and the absorbance at peak wavelength was determined by absorbance scan immediately and after incubation at room temperature for 24 hours. Results for four nitric oxide generators are given below.

TABLE 5

| Compound | Peak (nm) | Initial Abs. | 24-hour Abs. | % Decrease |
|---|---|---|---|---|
| M-DEA/NO | 234.4 | 3.454 | 3.020 | 14 |
| MOM-IPA/NO | 233.0 | 3.530 | 3.340 | 5 |

EXAMPLE V

In vivo evidence of nitric oxide generation.

A growth-inhibition curve experiment was conducted to determine the dose-dependent effects on incubating various pathogenic microbes in the presence of increasing concentrations of nitric oxide generators.

The experimental results shown in Table 5 show the dosages at which growth of each of *Candida albicans, Francisella tularensis*, and *Leishmania major* is inhibited 50% ($IC_{50}$). Selected microorganisms were cultured in defined liquid growth media suitable for each microbe that contained the indicated nitric oxide generator. Control cultures were inoculated simultaneously into defined liquid growth media without any nitric oxide generator. The nitric oxide generator compounds initially were dissolved in 10 mM NaOH, then added to the media to the desired concentration.

TABLE 6

In vivo effects of nitric oxide generators on microbial growth.

| Compound | Microbe | $IC_{50}(M)$ |
|---|---|---|
| DETA/NO | Candida albicans | $<10^{-4}$ |
|  | Francisella tularensis | $<10^{-4}$ |
|  | Leishmania major | $<10^{-2}$ |
| SPER/NO | Candida albicans | $<10^{-4}$ |
|  | Francisella tularensis | $<10^{-5}$ |
|  | Leishmania major | $<10^{-4}$ |

Other experiments have also shown killing of Mycobacterium strains.

EXAMPLE VI

In vivo evidence for the killing of macrophage-based pathogens by NO donors generators was demonstrated by the following experiments. Mice were inoculated with a lethal dose of a Gram-negative pathogen, *F. tularensis*, by intraperitoneal injection (IP). Two days after inoculation, the indicated compounds were injected IP at a concentration of 200 μM. Usually, the mean time to death of the control mice inoculated with *F. tularensis* was seven days. Mice surviving for a substantial (4 weeks) amount of time past the controls, mean time to death were considered survivors. Table 7 is a summary of the results for two of four experiments. As shown in experiment #1, we found that 80% of the mice challenged with a lethal dose of *F. tularensis* were protected when treated with the nitric oxide donor/generator, MOM—DEA/NO. The anti-microbial effects of MOM—DEA/NO were not found to be significant in two subsequent experiments. Unfortunately, in one of the two subsequent experiments, we found that the control mice displayed partial protection (i.e., an extended mean time to death) without the addition of NO donors/generators. Therefore, this experiment remains inconclusive. Future experiments will need to be performed to verify these initial observations.

TABLE 7

In vivo effects of nitric oxide generators: protection against *Francisella tularensis*

| Compound | #Dead/Total | % Protected |
|---|---|---|
| experiment #1 |  |  |
| DEA/NO | 5/5 | 0 |
| Acetoxy-DEA/NO | 2/4 | 50 |
| MOM-DEA/NO | 1/5 | 80 |
| control | 4/4 | 0 |
| experiment #2 |  |  |
| MOM-DEA/NO | 1/5 | 80 |
| control | 3/5 | 40 |

ENCAPSULATED. Since a primary goal is to target nitric oxide releasing compounds (NONOates, i.e., compounds containing the $N_2O_2^-$ group) to infected cell, and thereby concentrate high levels of NO near the infectious agent, we have hypothesized that liposomes may facilitate this process because they are readily taken up by macrophages. To determine whether liposomes would enhance the uptake of these NONOates by macrophages, we compared the amount of NO released by macrophages after incubating these cells with either liposome-encapsulated NONOates or non-encapsulated NONOates. In this example, we found the unexpected result that macrophages released 71% and 78% more NO after exposure to liposomes containing SPER/NO and DETA/NO, respectively, than macrophages treated with non-encapsulated SPER/NO and DETA/NO.

As shown below, significant amounts of NO were detected in cultures of macrophage cells previously treated with liposome-encapsulated NONOates, whereas non-encapsulated NONOates were not taken up by these cells. This indicates that the liposomes were effective at targeting NONOates to macrophages and enhancing the uptake of NONOates by macrophages. The accumulated $NO_2^-$ in the culture medium, a surrogate marker for NO, is the result of the oxidation of NO from NONOates, since liposomes alone (control) did not stimulate $NO_2^-$ production by the macrophages. Furthermore, the addition of a specific inhibitor of endogenous NO had no effect on reducing $NO_2^-$ in any of the treatment groups. Therefore, these data indicate that liposomes serve as a carrier of NONOates to macrophages, the target cells of many intracellular pathogens.

TABLE 8

Targeting and concentrating exogenous NO in macrophages:
Effects of liposome-encapsulated NONOates[1]

| Treatment | Compound | $NO_2$—(nmol/ml) |
|---|---|---|
| LIPOSOME-ENCAPSULATED | | |
| | SPER/NO | 5 ± 1 |
| | DETA/NO | 11 ± 4 |
| | control | 0 |
| NON-ENCAPSULATED | | |
| | SPER/NO | 1 ± 1 |
| | DET/NO | 0 |
| | control | 0 |

[1]50 μM of indicated NONOates, either encapsulated or non-encapsulated, were added to cultures containing 105 macrophages/ml. After a 1 hr incubation, microphage cells were washed extensively to remove all non-cell associated liposome-encapsulated NONOates and non-encapsulated NONOates. After 24 hrs, culture medium was assessed for $NO_2$—, the oxidative end-product and surrogate marker of NO.

NON-ENCAPSULATED. Upon further evaluation of all 20 NONOates listed in Table 1, SPER/NO, DETA/NO, and acetoxy-DEA/NO were found to be 6.7-, 7.2-, and 8.9-times, respectively, more effective at blocking *Leishmania major* growth in vitro than glucantime. Glucantime is the current and approved drug of choice for treatment of Leishmaniasis in humans. Assessment of inhibition of parasite growth in vitro is based on comparing equivalent molar concentrations of NONOates and glucantime. All other NONOates tested were significantly less effective at directly inhibiting the growth of Leishmania in vitro. As shown in Table 9 below, another parasite which is susceptible to NO is *Plasmodium falciparum*, the causative agent of human malaria. Since there are no relevant anti-malarial agents to compare, we determined the $IC_{50}$ and $IC_{90}$ in vitro. Again, all 20 compounds were tested, and consistent with the Leishmania survey only SPER/NO and acetoxy-DEA/NO were effective.

TABLE 9

Anti-malaria in vitro screen:
effects of NONOates

| Compound | Clone | $IC_{50}$ (ng/ml) | $IC_{90}$ (ng/ml) |
|---|---|---|---|
| SPER/NO | W2 | 5646 | 10020 |
| | D6 | 5306 | 9526 |
| DETA/NO | W2 | 37 | 94 |
| | D6 | 4826 | 10124 |
| Acetoxy-DEA/NO | W2 | 17749 | 19165 |
| | D6 | 267 | 295 |

The antimalaria activity was studied using modifications of the procedures described by Desjardins et al. (1979), 16:710, Chulay et al. (1983) Exp. Parasitol 55:138 and Milhous et al. (1985) Antimicrobial Agents Chemother. 27:525. The system is limited to the assessment of drug activity against the erythrocytic asexual life cycle of two *P. falciparum* clones from CDC/Indochina III (W2) and CDC/Sierra Leone I (D6) as noted in the table. Both W2 and D6 are used because of their differences in susceptibility to various drugs (i.e., chloroquine). Surprisingly, DETA/NO was found to be substantially more potent than SPER/NO and acetoxy-DEA/NO in W2. Acetoxy-DEA/NO was found to be substantially more potent than SPER/NO and DETA/NO in D6.

Additional modifications for various conditions encountered in the use of this invention that are obvious to those skilled in the art are within the scope and spirit of the invention.

We claim the following:

1. A method of killing or inhibiting the proliferation of infectious or pathogenic microorganisms in a human or an animal, which method comprises administering to said human or animal a compound capable of releasing nitric oxide in an aqueous solution such that said infectious or pathogenic microorganisms are exposed to nitric oxide and such that the proliferation of said infectious or pathogenic microorganism is inhibited or said infectious or pathogenic microorganism is killed.

2. The method of claim 1, wherein said compound is capable of releasing nitric oxide under physiological conditions.

3. The method of claim 2, wherein said compound is a nitric oxide/nucleophile complex or a derivative thereof.

4. The method of claim 3, wherein said compound is a nitric oxide/nucleophile complex.

5. The method of claim 4, wherein said compound contains the anionic moiety $X[N(O)NO]^-$, where X is a nucleophile residue.

6. The method of claim 5, wherein X is selected from the group consisting of spermine, 3-(n-propylamino) propylamine, diethylamine, isopropylamine, and oxyanion.

7. The method of claim 3, wherein said compound is $(CH_3CH_2)_2N[N(O)NO]Na$.

8. The method of claim 3, wherein said compound is of the formula V

wherein $R_1$ and $R_2$ are independently selected from the group consisting of a straight chain or branched chain $C_1$–$C_{12}$ alkyl group and a benzyl group, $M^{+x}$ is a pharmaceutically acceptable cation, and x is the valence of the cation.

9. The method of claim 3 wherein said compound comprises a nitric oxide/nucleophile adduct bound to a polymer.

10. The method of claim 1 wherein the compound capable of releasing nitric oxide in an aqueous solution is encapsulated within a vesicle.

11. The method of claim 10, wherein the vesicle is a liposome.

12. The method of claim 1, wherein the microorganism is exposed to the compound capable of releasing nitric oxide in an aqueous solution wherein the route of administration of said compound is selected from the group consisting of aerosolization into the respiratory system, intraperitoneal injection, injection into a tumor, cutaneous injection, subcutaneous injection, topical application, and intracranial injection.

13. The method of claim 1, wherein said microorganisms are exposed to said nitric oxide releasing compound in an amount sufficient to inhibit the proliferation of said microorganisms.

14. The method of claim 1, wherein said compound is administered in a therapeutically effective amount with a pharmaceutically acceptable carrier to an animal.

15. The method of claim 3, wherein said compound is $(CH_3)_2CHNH[N(O)NO]$ Na.

16. The method of claim 3, wherein said compound is $CH_3CH_2CH_2N[N(O)NO]^-CH_2CH_2CH_2NH_3^+$.

17. The method of claim 3, wherein said compound is $H_2N(CH_2)_3NH_2^+(CH_2)_4N[N(O)NO]^-(CH_2)_3NH_2$.

18. The method of claim 3, wherein said compound is $NaO[N(O)NO]Na$.

19. The method of claim 3, wherein said compound is of the formula I

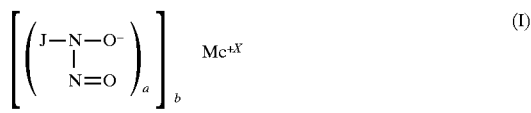

wherein J is an organic or inorganic moiety, $M^{+X}$ is a pharmaceutically acceptable cation, where x is the valence of the cation, a is 1 or 2, and b and c are the smallest integers that result in a neutral compound, or pharmaceutically acceptable salts or derivatives thereof, with the proviso that the compound is not a salt of alanosine or dopastin, or pharmaceutically acceptable salts or derivatives thereof.

20. The method of claim 3, wherein said compound is of the formula I

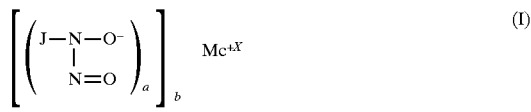

wherein J is an organic or inorganic moiety, which is not linked to the nitrogen of the remainder of the complex through a carbon atom, $M^{+X}$ is a pharmaceutically acceptable cation, where x is the valence of the cation, a is 1 or 2, and b and c are the smallest integers that result in a neutral compound, or pharmaceutically acceptable salts or derivatives thereof, with the proviso that the compound is not a salt of alanosine or dopastin, or pharmaceutically acceptable salts or derivatives thereof.

21. The method of claim 3, wherein said compound is of the formula

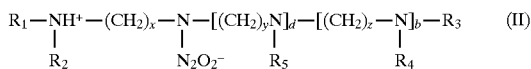

wherein b and d are the same or different and may be zero or one, $R_1$, $R_2$, $R_3$, $R_4$, and $R_5$ are the same or different and may be hydrogen, $C_{3-8}$ cycloalkyl, $C_1-C_{12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12.

22. The method of claim 3, wherein said compound is of the formula

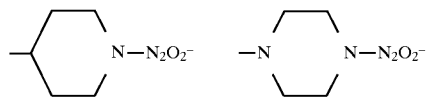

wherein B is $R_6$ and $R_7$ are the same or different and may be hydrogen, $C_{3-8}$ cycloalkyl, $C_1-C_{12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, f is an integer from 0 to 12, with the proviso that when B is the substituted piperazine moiety

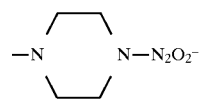

then f is an integer from 2 to 12, or a pharmaceutically acceptable salt or derivative thereof.

23. The method of claim 3, wherein said compound is of the formula

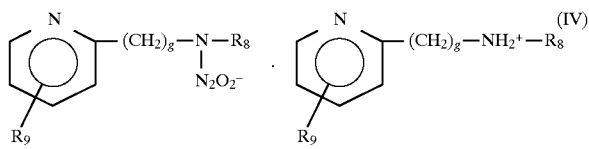

wherein $R_8$ is hydrogen, $C_{3-8}$ cycloalkyl, $C_1-C_{12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, $R_9$ is hydrogen or a $C_1-C_{12}$ straight or branched chain alkyl, and g is 2 to 6, or a pharmaceutically acceptable salt or derivative thereof.

24. The method of claim 3, wherein said compound is of the formula

wherein M is a pharmaceutically acceptable metal, or where x is at least two, a mixture of two different pharmaceutically acceptable metals, L is a ligand different from ($R^1R^2N$—$N_2O_2$) and is bound to at least one metal, $R^1$ and $R^2$ are each organic moieties and may be the same or different, x is an integer of from 1 to 10, x' is the formal oxidation state of the metal M, and is an integer of from 1 to 6, y is an integer of from 1 to 18, and where y is at least 2, the ligands L may be the same or different, z is an integer of from 1 to 20, and K is a pharmaceutically acceptable counterion to render the compound neutral to the extent necessary, or a pharmaceutically acceptable salt or derivative thereof.

25. The method of claim 3, wherein said compound is of the formula

wherein R is $C_{2-8}$ lower alkyl, phenyl, benzyl, or $C_{3-8}$ cycloalkyl, any of which R groups may be substituted by one to three substituents, which are the same or different, selected from the group consisting of halo, hydroxy, $C_{1-8}$ alkoxy, $-NH_2$, $-C(O)NH_2$, $-CH(O)$, $-C(O)OH$, and $-NO_2$, X is a pharmaceutically acceptable cation, a pharmaceutically acceptable metal center, or a pharmaceutically acceptable organic group selected from the group consisting of $C_{1-8}$ lower alkyl, $-C(O)CH_3$, and $-C(O)NH_2$, and y is one to three, consistent with the valence of X, or a pharmaceutically acceptable salt or derivative thereof.

26. The method of claim 3, wherein said compound is of the formula

(VIII)

wherein $R_1$ and $R_2$ are independently chosen from $C_1$–$C_{12}$ straight chain alkyl, $C_1$–$C_{12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$ together with the nitrogen atom to which they are bonded form a heterocyclic group, and $R_3$ is a group selected from $C_1$–$C_{12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_1$–$C_{12}$ unsubstituted or substituted acyl, sulfonyl and carboxamido; or $R_3$ is a group of the formula $-(CH_2)n-ON=N(O)NR_1R_2$, wherein n is an integer of 2–8, and $R_1$ and $R_2$ are as defined above.

* * * * *